(12) United States Patent
Hirata et al.

(10) Patent No.: US 7,860,577 B2
(45) Date of Patent: Dec. 28, 2010

(54) INTRACRANIAL ELECTRODE AND METHOD FOR PRODUCING SAME

(75) Inventors: Masayuki Hirata, Suita (JP); Toshiki Yoshimine, Suita (JP); Youichi Saitoh, Suita (JP); Takufumi Yanagisawa, Suita (JP); Testu Goto, Suita (JP); Yoshihiro Watanabe, Komae (JP); Toshiaki Saito, Komae (JP)

(73) Assignee: Osaka University, Osaka (JP)

( * ) Notice: Subject to any disclaimer, the term of this patent is extended or adjusted under 35 U.S.C. 154(b) by 135 days.

(21) Appl. No.: 12/378,695

(22) Filed: Feb. 18, 2009

(65) Prior Publication Data

US 2009/0228066 A1    Sep. 10, 2009

(30) Foreign Application Priority Data

Aug. 22, 2007  (JP) .............................. 2007-216461

(51) Int. Cl.
*A61N 1/00* (2006.01)
(52) U.S. Cl. ...................................................... 607/116
(58) Field of Classification Search ................. 600/378; 607/116, 117, 45, 48; 264/219
See application file for complete search history.

(56) References Cited

U.S. PATENT DOCUMENTS 4,228,799 A * 10/1980 Anichkov et al. ........... 606/130
5,044,368 A    9/1991 Putz
5,961,909 A * 10/1999 Iverson ....................... 264/219

FOREIGN PATENT DOCUMENTS

JP    2002-014610 A    1/2002
JP    2002-040928 A    2/2002

OTHER PUBLICATIONS

M. Hirata et al., "Hierarchical network in the human sensorimotor cortex: coherence analysis using supragyral and intrasulcal surface electrodes." The 29th Annual Meeting of the Japan Neuroscience Society; Neuroscience 2006 in Kyoto Japan. 0S2P-7-11 Jul. 20,2006.
Y. Saitoh et al., "Primary motor cortex stimulation within the central sulcas for trating deafferation pain." Acta Neurochir [Suppl.] vol. 87, pp. 149-152, (2003).
T. Yanagisawa et al., "Neural decoding using gyral and intrasulcal electrocorticograms." Neuroimage vol. 45, pp. 1099-1106, (2009).

* cited by examiner

*Primary Examiner*—George Manuel
*Assistant Examiner*—Robert N Wieland
(74) *Attorney, Agent, or Firm*—Edwards Angell Palmer & Dodge LLP; David G. Conlin; Catherine J. Toppia

(57) ABSTRACT

With use of three-dimensional data of a brain shape, a mold for forming a sheet-shaped structure having a three-dimensional shape of the gyrus or sulcus surface, or the interhemispheric fissure or interlobar fissure surface is formed. With use of the mold, a sheet-shaped silicone structure 2 having a three-dimensional shape of the gyrus or sulcus surface, or the interhemispheric fissure or interlobar fissure surface is formed. An electrode 3 is arranged on at least one side of the silicone structure 2. With this configuration, an intracranial electrode 1 in which the electrode 3 is arranged on the sheet-shaped silicone structure 2 having the three-dimensional shape of the gyrus or sulcus surface, or the interhemispheric fissure or interlobar fissure surface can be produced.

17 Claims, 6 Drawing Sheets

INTRACRANIAL ELECTRODE AND METHOD FOR PRODUCING SAME

TECHNICAL FIELD

The present invention relates to an intracranial electrode to be placed intracranially and a method for producing the same. Especially, the present invention relates to an intracranial electrode having a three-dimensional shape of the gyrus or sulcus surface, or the interhemispheric fissure or interlobar fissure surface, and a method for producing the same.

BACKGROUND ART

A conventional intracranial electrode is used for measuring an intracranial brain signal directly, examining a brain function by applying electrical stimulation to the brain, and treating intractable pain or involuntary movement. A typical intracranial electrode can be roughly classified into (1) a deep brain stimulation electrode which is inserted deep into the brain and (2) a subdural electrode which is placed on the brain surface.

In the deep brain stimulation electrode, generally, electrodes are arranged at even intervals on a thin tube. Such a deep brain stimulation electrode is used for measuring brain signals and electrical stimulation in a deep part of the brain. On the other hand, in the subdural electrode, generally, electrodes made of such as platinum are fixed on one side of an electrode sheet formed from such as silicone. Such a subdural electrode is used for measuring a brain signal and electrical stimulation on the brain surface.

More specifically, a deep brain stimulation electrode includes such as a lead wire type electrode which is used in deep brain stimulation for a parkinsonian patient. Moreover, a subdural electrode includes such as an intracranially implantable diagnostic electrode in which an electrode is held in intermembrane space of a silicone double membrane whose thickness is 1 mm or less (e.g. see Patent Literature 1).

Moreover, a double-sided electrode is commercially available as another intercranial electrode. In the double-sided electrode, electrodes are provided on both sides of a silicone sheet. The double-sided electrode is used for being inserted into the interhemispheric fissure (section between right and left cerebral hemispheres), and measuring brain signals from right and left cerebral hemispheres.

Moreover, a conventional electrode, which includes a structure having a plurality of electrodes therein and arranged along a tissue surface of such as a heart, has been used (e.g. see Patent Literature 2). Note that, the structure is produced by spraying a material on a surface of a mold having a shape of a target tissue. Further, positions of the electrodes in the structure are predetermined on the mold.

The cerebral cortex can be divided into two regions. One region is the brain surface called "gyri", and the other region is a recess in the brain surface called "sulci". The sulci have an area three times larger than the gyri. Therefore, the sulci are considered to serve an important role for a brain function.

In these years, it is experimentally proved that, a brain signal in the sulcus has a drastically different characteristic from a brain signal in the gyrus in some cases (e.g. see Non Patent Literatures 1 and 3). Especially, it is proved that, depending on kinds of motion, brain signal characteristics are drastically different from one another in the sulcus and the gyrus in the primary motor area of the cerebral cortex.

Citation List
Patent Literature 1
U.S. Pat. No. 5,044,368 A (Publication Date: Sep. 9, 1991)
Patent Literature 2
U.S. Pat. No. 5,961,909 A (Publication Date: Oct. 5, 1999)
Non Patent Literature 1
M. Hirata et al., Hierarchical network in the human sensorimotor cortex: coherence analysis using supragyral and intrasulcal surface electrodes, in Abstracts of The 29th Annual Meeting of the Japan Neuroscience Society (2006)
Non Patent Literature 2
Y. Saitoh et al., Primary motor cortex stimulation within the central sulcus for treating deafferentation pain, Acta Neurochir [Suppl.]87:149-152, (2003)
Non Patent Literature 3
T. Yanagisawa et al., Neural decoding using gyral and intrasulcal electrocorticograms. Neuroimage (in press)

As mentioned above, in these years, importance of the sulcus for a brain function has been understood. In order to analyze a more detailed role of the sulcus for a brain function, it is necessary to measure an intersulcus brain signal, and to locally apply electrical stimulation to the sulcus. For example, Non Patent Literature 2 recites that, for treating intractable pain, the motor area within the central sulcus is stimulated by an electrode arranged in the sulcus.

However, at present, measurement of a brain signal and electrical stimulation in the sulcus are rarely performed. Moreover, there is no effective electrode for the measurement and the stimulation. For example, electrodes recited in Patent Literature 1 and Non Patent Literature 2 have planar shapes, and besides, the electrodes are hard. Therefore, if the electrode is placed in the sulcus, a cerebral dysfunction would possibly occur due to pressure applied by the electrode. Moreover, even in a case where the electrode is placed on a surface of the brain, the electrode sheet would possibly apply pressure on the brain when the electrode (sheet) is large. Further, an electrode placed on the brain surface has an advantage that spatial resolution can be improved because the electrode measures a brain signal from the brain surface. However, in the conventional electrodes, an interval between electrodes is approximately 1 cm in general, and it is hard to regard their spatial resolution as high enough.

Moreover, a conventional method for producing an electrode has a problem in that the method cannot produce a thin electrode having a uniform thickness. For example, the method in Patent Literature 2 has a problem in that a structure is formed by simply spraying a material on a mold, whereby a thickness of the structure cannot be even. Further, the method in Patent Literature 2 also has a problem in that a structure is formed after positions of electrodes are predetermined, and this leads to low positional flexibility of the electrodes.

SUMMARY OF INVENTION

The present invention is achieved in consideration of the above problems, and an object of the present invention is to provide (i) an intracranial electrode which can be placed intracranially with smaller pressure on the brain and (ii) a method for producing the intracranial electrode.

In order to attain the object, a method for producing an intracranial electrode of the present invention includes steps of: obtaining three-dimensional data of a brain shape; with use of the three-dimensional data, forming a sheet-shaped mold having a three-dimensional shape of the gyrus or sulcus surface, or the interhemispheric fissure or interlobar fissure surface; with use of the mold, forming a sheet-shaped structure which (i) is made of a biocompatible material and (ii) has the three-dimensional shape of the gyrus or sulcus surface, or the interhemispheric fissure or interlobar fissure surface; and arranging an electrode on at least one side of the structure.

With the configuration, it is possible to produce an intracranial electrode including a sheet-shaped structure which (i) is made of a biocompatible material, (ii) has a three-dimensional shape of the gyrus or sulcus surface, or the interhemispheric fissure or interlobar fissure surface, and (iii) is provided with an electrode. Thus produced intracranial electrode has the three-dimensional shape of the gyrus or sulcus surface, or the interhemispheric fissure or interlobar fissure surface.

With the configuration, pressure on the brain can be smaller even when the intracranial electrode is placed on the gyrus or sulcus surface, or the interhemispheric fissure or interlobar fissure surface. Therefore, with the configuration, it is possible to produce an intracranial electrode which can detect a brain signal from the gyrus or sulcus surface, or the interhemispheric fissure or interlobar fissure surface without causing disturbance or damage to the brain.

Moreover, a structure, which serves as a base material of the intracranial electrode in the configuration, is made of a biocompatible material. This makes it possible to produce an intracranial electrode which does not cause a negative effect on a living body even when the intracranial electrode is placed intracranially.

Moreover, the configuration includes a step of obtaining three-dimensional data of a brain shape. This makes it possible to produce intracranial electrodes which suit brains of different shapes respectively.

Moreover, in the configuration, a structure can be formed with use of a mold. Therefore, a large amount of structures, in which a surface shape of the brain is reflected precisely, can be produced easily. Moreover, a large amount of structures, which also have a desired shape (e.g. a grooved wiring route for electrode wiring), can be produced easily by further processing the mold.

The method for producing an intracranial electrode of the present invention is preferable to further include steps of: forming another mold which fits closely with a front side or a back side of the mold; arranging the biocompatible material between the mold and the another mold; and forming the sheet-shaped structure by pressing the mold and the another mold against each other with pressure.

In the configuration, a structure is formed by applying pressure on a biocompatible material between a pair of molds. This makes it possible to form a structure (i) that has a precise shape of the brain surface and (ii) whose thickness is uniform and thin.

In the method for producing an intracranial electrode of the present invention, the mold is preferable to be formed by attaching a sheet-shaped material to a surface of a model with pressure, the model having the brain shape formed with use of the three-dimensional data.

This makes it possible to form a structure (i) that has a precise shape of the brain surface and (ii) whose thickness is uniform and thin.

In the method for producing an intracranial electrode of the present invention, it is preferable that the mold is formed by applying a material to a surface of a model having the brain shape formed with use of the three-dimensional data, and subsequently pressing a supplemental mold to the surface of the model with pressure, the supplemental mold covering the material.

This makes it possible to form a structure (i) that has a precise shape of the brain surface and (ii) whose thickness is uniform and thin.

In the method for producing an intracranial electrode of the present invention, the mold is preferable to be formed by a three-dimensional printer or a three-dimensional optical molding machine with use of the three-dimensional data.

A three-dimensional printer and a three-dimensional optical molding machine can precisely reproduce an imperceptible and extremely complex brain surface. This makes it possible to form a structure which has further precise three-dimensional shape of the gyrus or sulcus surface, or the interhemispheric fissure or interlobar fissure surface.

The method for producing an intracranial electrode of the present invention is preferable to include steps of: with use of the mold, forming a first sheet-shaped member which (i) is made of a biocompatible material and (ii) has a three-dimensional shape of the gyrus or sulcus surface, or the interhemispheric fissure or interlobar fissure surface; with use of the mold, forming a second sheet-shaped member which (i) is made of a biocompatible material and (ii) has a three-dimensional shape of the gyrus or sulcus surface, or the interhemispheric fissure or interlobar fissure surface; and forming the sheet-shaped structure by attaching the first sheet-shaped member and the second sheet-shaped member together.

In the configuration, a plurality of sheet-shaped members is laminated, and the electrode is provided in a hole in at least one of outermost sheet-shaped members. This allows production of an intracranial electrode which can contact with the gyrus or sulcus surface, or the interhemispheric fissure or interlobar fissure surface when the intracranial electrode is placed on the gyrus or sulcus surface, or the interhemispheric fissure or interlobar fissure surface.

Further, in the configuration, a wiring connected with the electrode can be provided in any of interlayer sections of a laminated structure including a plurality of the sheet-shaped members. Therefore, an intracranial electrode, which causes neither disturbance nor damage to the brain by the wiring connected with the electrode, can be produced.

In the configuration, a structure can be formed with use of a mold. Therefore, a large amount of structures, in which a surface shape of the brain is reflected precisely, can be produced easily. Moreover, a large amount of structures, which also has a desired shape (e.g. a grooved wiring route for electrode wiring), can be produced easily by further processing the mold.

In the method for producing an intracranial electrode of the present invention, the mold for forming the first sheet-shaped member is preferable to be different from the mold for forming the second sheet-shaped member.

In the configuration, a second sheet-shaped member can be formed in consideration of a shape of a first sheet-shaped member. This makes it possible to form a pair of sheet-shaped members which can be attached together more firmly. This makes it possible to produce an intracranial electrode which fits more closely with the brain surface.

In the method for producing an intracranial electrode of the present invention, the three-dimensional data of the brain shape is preferable to be obtained based on a brain image obtained by magnetic resonance imaging.

In the configuration, an image obtained by magnetic resonance imaging is used as a brain image for obtaining the three-dimensional data of the brain shape. Magnetic resonance imaging can obtain a high-resolution brain image. This improves precision of the three-dimensional data.

In the method for producing an intracranial electrode of the present invention, the electrode is preferable to be provided at a position at which the electrode will not contact with a blood vessel. In other words, the electrode is preferable not to be provided at a position at which the electrode will contact with a blood vessel.

In the configuration, an electrode does not contact with a prominent blood vessel on the brain surface. This allows an intracranial electrode to fit with the brain surface more closely. Moreover, the intracranial electrode does not cause hematogenous disorder because the electrode does not apply pressure on a blood vessel. This improves safety of the intracranial electrode.

The method for producing an intracranial electrode of the present invention is preferable to include a step of: in the sheet-shaped structure, forming a recess at a position which corresponds to a blood vessel on the brain surface.

The configuration can prevent an intracranial electrode from applying pressure on a blood vessel of the brain.

In order to attain the object, an intracranial electrode of the present invention includes: a structure which (i) has a sheet-shape and (ii) is made of a biocompatible material, the structure having a three-dimensional shape of the gyrus or sulcus surface, or the interhemispheric fissure or interlobar fissure surface; and the structure including at least one electrode.

In the configuration, the intracranial electrode has a three-dimensional shape of the gyrus or sulcus surface, or the interhemispheric fissure or interlobar fissure surface. This allows the intracranial electrode to fit with the brain surface closely when the intracranial electrode is placed on the gyrus or sulcus surface, or the interhemispheric fissure or interlobar fissure surface. This reduces pressure on the brain by the intracranial electrode. This makes it possible to detect a brain signal from the gyrus or sulcus surface, or the interhemispheric fissure or interlobar fissure surface without causing disturbance or damage to the brain.

Moreover, in the configuration, the intracranial electrode can have a shape which fits with the brain surface closely. Therefore, a brain signal can be detected with high precision and high sensitivity.

Further, the structure (base material) of the intracranial electrode is made of a biocompatible material. This can prevent a negative effect on a living body even when the intracranial electrode is placed intracranially.

In the intracranial electrode of the present invention, it is preferable that: the structure includes at least a first layer and a second layer; the structure has a multilayered structure whose outermost layers are the first layer and the second layer respectively; at least one hole is formed in at least one of the first layer and the second layer; and the electrode is provided in the hole.

In the configuration, the structure has a multilayered structure including at least the first layer and the second layer. Moreover, the first layer and the second layer are arranged outermost of the multilayered structure. Further, a hole is formed in at least one of the first layer and the second layer.

In the first layer and the second layer, the electrode is provided in a region where the hole is formed. Therefore, when the intracranial electrode is placed on the gyrus or sulcus surface, or the interhemispheric fissure or interlobar fissure surface, the electrode can contact with the gyrus or sulcus surface, or the interhemispheric fissure or interlobar fissure surface. With the configuration, it is possible to detect a brain signal from the gyrus or sulcus surface, or the interhemispheric fissure or interlobar fissure surface.

Moreover, in the configuration, a wiring connected with the electrode can be provided in any of interlayer sections of the multilayered structure. This can prevent disturbance or damage to the brain caused by the wiring connected with the electrode.

In the intracranial electrode of the present invention, it is preferable that the electrodes are provided on both sides of the structure.

Both sides (front side and back side) of an intracranial electrode can contact with the brain surface when the intracranial electrode is placed on the gyrus or sulcus surface, or the interhemispheric fissure or interlobar fissure surface. Therefore, with the configuration, brain signals can be detected by both sides of the intracranial electrode. This makes it possible to detect a brain signal efficiently from a distinct region in the gyrus or sulcus surface, or the interhemispheric fissure or interlobar fissure surface by placing only one intracranial electrode on the gyrus or sulcus surface, or the interhemispheric fissure or interlobar fissure surface.

In the intracranial electrode of the present invention, it is preferable that: the structure has a region in which a plurality of electrodes is arranged in high density; and intervals between the adjacent electrodes in the region are in a range of 0.3 mm to 10 mm.

The brain surface has a complex shape with undulating. In some cases, such brain surface has further complex shape depending on regions. The more a shape of brain surface becomes complex, the less closely the structure fits with the brain surface. However, in the configuration, even if sensitivity of an electrode in a spot is decreased because a structure cannot fit with the brain surface closely at the spot, another electrode can detect a brain signal with high sensitivity. As a result, with the configuration, a brain signal can be detected efficiently from a whole target brain surface.

In the intracranial electrode of the present invention, the electrode is preferable to be provided at a position at which the electrode will not contact with a blood vessel. In other words, the electrode is preferable not to be provided at a position at which the electrode will contact with a blood vessel.

In the configuration, the electrode does not contact with a prominent blood vessel on the brain surface. This allows the intracranial electrode to fit with the brain surface more closely. Moreover, the intracranial electrode does not cause hematogenous disorder because the electrode does not apply pressure on a blood vessel. This improves safety of the intracranial electrode.

In the intracranial electrode of the present invention, it is preferable that, in the sheet-shaped structure, a recess is formed at a position which corresponds to a blood vessel on the brain surface.

The configuration can prevent the intracranial electrode from applying pressure on a blood vessel of the brain.

In order to attain the objects, brain treatment with electrical stimulation of the present invention, wherein: electrical stimulation is applied to the gyrus or sulcus surface, or the interhemispheric fissure or interlobar fissure surface by using any one of the intracranial electrodes.

As described above, an intracranial electrode of the present invention can effectively detect a brain signal from a target region of the brain surface. Moreover, the intracranial electrode of the present invention can apply electrical stimulation to a target region of the brain surface effectively. More specifically, a treatment for such as pain can be performed effectively with the configuration.

For a fuller understanding of the nature and advantages of the invention, reference should be made to the ensuing detailed description taken in conjunction with the accompanying drawings.

DESCRIPTION OF EMBODIMENTS

An intracranial electrode of the present invention may be such electrodes that are used for sensing a brain signal and for applying electrical stimulation to the brain. However, the present invention is not limited to such electrodes. The present invention is described below via embodiments, to which the present invention is not limited.

First Embodiment

An embodiment of the present invention is explained below with reference to FIGS. 1, 2(a), 2(b), and 4. However, the present invention is not limited to the present embodiment.

Figure 1:
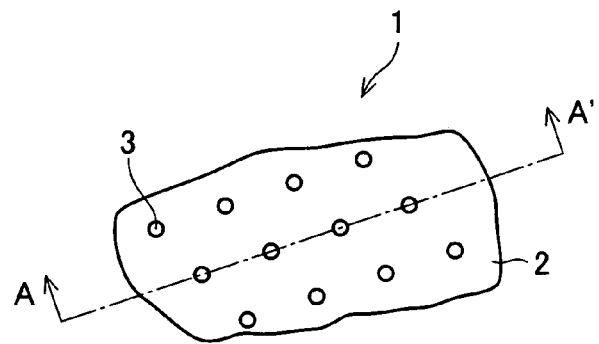
FIG. 1 is a top view illustrating an intracranial electrode of the embodiment.

As shown in FIG. 1, an intracranial electrode 1 of the present embodiment includes a silicone structure 2 (structure) and an electrode 3. The silicone structure 2 is a sheet-shaped structure which has a three-dimensional shape of the gyrus or sulcus surface, or the interhemispheric fissure or interlobar fissure surface.

Note that, for convenience of explanation, the gyrus or sulcus surface or the interhemispheric fissure or interlobar fissure surface sometimes represented as a "brain surface" in this specification.

In the present embodiment, the silicone structure 2 is used as a structure which functions as a base material of the intracranial electrode. However, the present invention is not limited to this. More specifically, the structure may be formed from a biocompatible material other than a silicone polymer (i.e. organosiloxanes such as dimethyl polysiloxane).

Although the biocompatible material is not limited especially, examples of the biocompatible material are polyurethane, polyamide, parylene, a fluorine polymer such as Teflon (registered trademark), polyolefin such as polyethylene and polypropylene, collagen, chitin, polyvinylpyrrolidone alginate, polyethylene glycol, polyethylene oxide, polyvinyl alcohol, polyglycol lactic acid, polylactic acid, polycaprolactone, polyamino acid, and hydrogel such as carboxymethylcellulose.

The biocompatible material is preferable to be a soft biocompatible material (such as silicone or parylene). Further, a soft silicone polymer is a most preferable material as the biocompatible material. With the configuration, pressure on the brain can be further reduced. Moreover, the configuration allows the intracranial electrode to adhere with the brain surface more closely, whereby a brain signal can be detected with higher sensitivity.

Moreover, the silicone structure 2 is a sheet-shaped structure. The silicone structure 2 is not especially limited in terms of its thickness but is preferably as thin as possible provided that the silicone structure 2 is endurable in practical use. In general, the thickness is preferable to be in a range of 0.02 mm to 0.1 mm. With such a thin sheet-shaped structure, applied pressure on the brain by the intracranial electrode 1 can be smaller even when the intracranial electrode 1 is placed on the brain surface intracranially.

Figure 2:
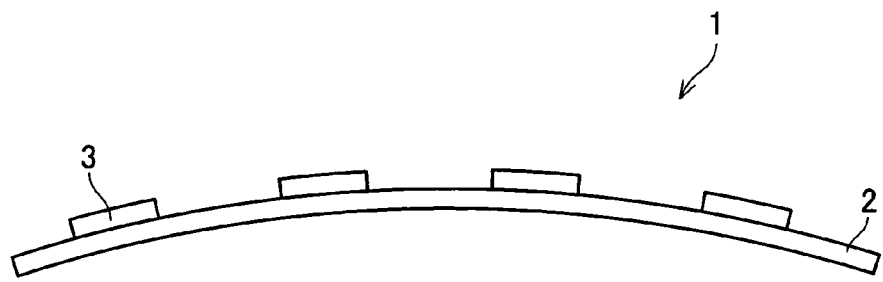
FIG. 2(a) is a cross-sectional view taken along line A-A', illustrating the intracranial electrode in FIG. 1.
FIG. 2(b) is a cross-sectional view illustrating an intracranial electrode of another embodiment.
Figure 2:
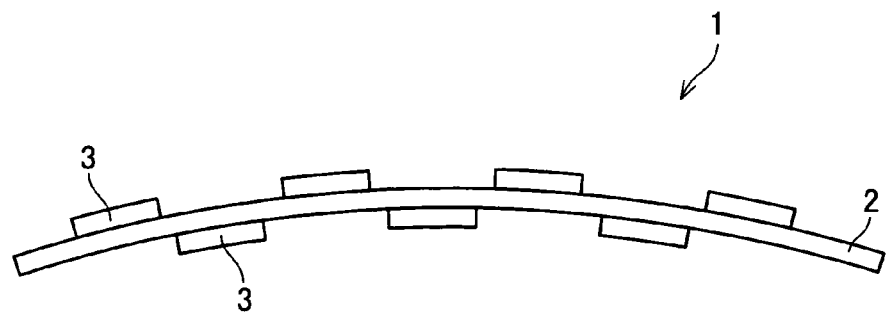

As shown in FIG. 2(a), the electrode 3 is arranged on one side of the silicone structure 2. Although the electrode 3 is arranged on only one side of the silicone structure 2 in the present embodiment as shown in FIG. 2(a), the present invention is not limited to this. That is, it is sufficient that the electrode 3 is provided on at least one side of the silicone structure 2. In other words, the electrode(s) 3 may be provided either on only one side of the sheet-shaped silicone structure 2, or on both sides (front side and back side) of the silicone structure 2 (e.g. see FIG. 2(b)). When the electrodes 3 are arranged on both sides of the silicone structure 2, each of the sides can contact with different regions of the brain surface respectively. As a result, different brain signals from different brain surfaces can be detected by one intracranial electrode 1 concurrently. Therefore, it can be said that the present embodiment can be utilized for inserting an electrode into the sulcus.

Moreover, the number of the electrode 3 arranged on the silicone structure 2 is not especially limited. Further, in a case where the electrodes 3 are arranged on both sides of the silicone structure 2, the number of the electrodes 3 arranged on each of front side and back side is also not especially limited. The numbers of the electrodes 3 arranged on each side may be either the same or different. Moreover, positions of the electrodes 3 arranged on each side are also not especially limited. The electrodes 3 on both sides may be arranged either symmetrically or asymmetrically.

Moreover, in a case where a plurality of the electrodes 3 is arranged on the silicone structure 2, an interval between each electrode 3 (i.e. a distance between the nearest electrodes) is not especially limited. More specifically, the electrodes 3 are preferable to be arranged on the silicone structure 2 with intervals in a range of 0.3 mm to 10 mm, more preferably, with intervals in a range of 1 mm to 5 mm, further preferably, with intervals in a range of 1 mm to 3 mm. When the electrode 3 is arranged with the intervals, a brain signal from the brain surface having an extremely complex shape can be detected with high efficiency and high sensitivity. Note that, a region of the silicone structure 2 on which the electrodes 3 are arranged with the intervals may be either a whole or a part of a surface of the silicone structure 2. The region (in which the electrodes are arranged in high density) on the silicone structure 2 is preferable to be a region corresponding to the brain surface having a complex surface shape when the intracranial electrode 1 is placed on the brain surface.

Moreover, an arrangement pattern of the electrodes 3 on the silicone structure 2 is not especially limited. However, it is preferable that the electrodes 3 are arranged on the silicone structure 2 so as not to contact with a main blood vessel on the brain surface when the intracranial electrode 1 is placed on the brain surface. Note that, such an arrangement pattern can be achieved by: identifying a position of a main blood vessel on the brain surface by such as a magnetic resonance image; and then arranging the electrodes 3 according to thus obtained positional information, so as to form the silicone structure 2.

Note that, the electrodes 3 may be arranged on the silicone structure 2 either in a plurality of lines or in a net-like pattern.

A material for the electrode 3 is not limited as long as the material is a metal or an alloy which can be used as an electrode. More specifically, examples of the material are platinum (Pt), titanium (Ti), and nitinol (NiTi).

Moreover, a shape and a size of the electrode 3 are not limited. The shape and the size may be determined as appropriate according to such as intervals between electrodes. More specifically, examples of the electrode 3 are a circular electrode in a range of ø0.2 mm to ø3 mm, and more preferably, a circular electrode in a range of ø0.5 mm to ø1.5 mm.

Here, a method for producing an intracranial electrode 1 is explained. The intracranial electrode 1 can be produced by a method including steps of: with use of three dimensional data of a brain shape, forming a mold for forming a sheet-shaped structure having a three-dimensional shape of the brain surface (hereinafter referred to as a "mold formation step (A)"); with use of the mold, forming a silicone structure 2 (hereinafter referred to as a "structure formation step (A)"); and arranging an electrode 3 on at least one side of the silicone structure 2 (hereinafter referred to as an "electrode arrangement step (A)").

Figure 4:
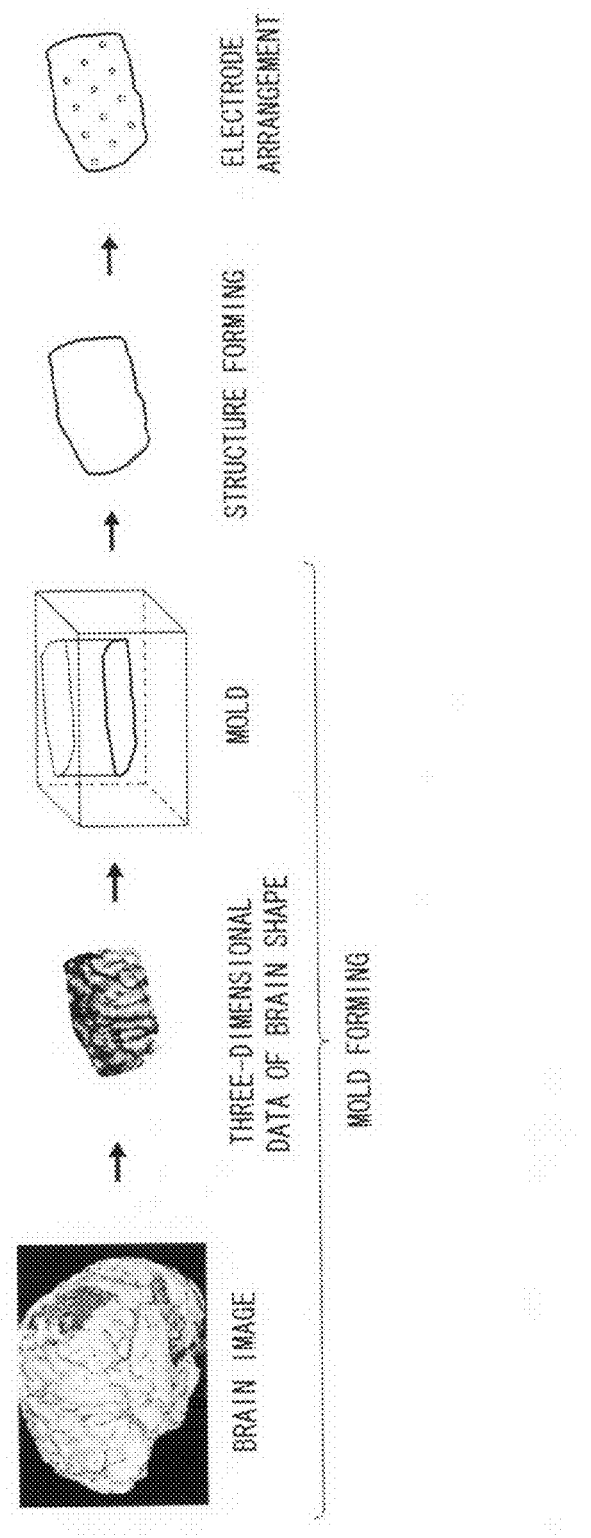
FIG. 4 is a view illustrating steps of a method for producing an intracranial electrode of the embodiment.

In the mold formation step (A), a mold is formed with use of three-dimensional data of a brain shape as shown in FIG. 4. The mold is used for forming a sheet-shaped structure in the three-dimensional shape of the brain surface. Although the three-dimensional data of the brain shape is not especially limited, it is preferable that the three-dimensional data of the brain shape is obtained from a person in whom the intracranial electrode 1 is to be placed.

When such three-dimensional data of a brain shape is used, the shape of the intracranial electrode 1 is consistent with the brain surface shape of the person in whom the intracranial electrode 1 is to be placed. With this configuration, it is possible further to reduce pressure on the brain when the intracranial electrode 1 is placed on the brain surface of the person in whom the intracranial electrode 1 is to be placed.

Moreover, the three-dimensional data of the brain shape is obtained based on a brain image obtained by a device which can obtain a brain image. How to obtain the brain image and how to obtain the three-dimensional data of the brain shape with use of the brain image are not limited.

In the present embodiment, the brain image is preferable to be obtained by magnetic resonance imaging (MRI). The MRI is suitable for capturing a high resolution brain image. Therefore, three-dimensional data of a brain shape with high precision can be obtained with use of a brain image obtained by the MRI. As a result, the silicone structure 2 can have a further precise three-dimensional shape of the brain surface. This further improves the similarity between the three-dimensional shapes of the intracranial electrode 1 and the brain surface.

Moreover, in the brain image obtaining method by use of the MRI, it is preferable that cross-sectional images of the brain are obtained with intervals in a range of approximately 0.5 mm to 1.5 mm. If MRI images are obtained with such intervals, highly precise three-dimensional data of a brain shape can be obtained.

Further, the brain image is preferable to be obtained in a state where a contrast medium is administered into a blood vessel. With the contrast medium, the blood vessel on the brain surface can be contrasted. Therefore, according to three-dimensional data of a brain shape obtained based on such a brain image, positions of the blood vessel on the brain surface can be located.

According to thus identified positional information of the blood vessel, the electrodes 3 can be arranged on the silicone structure 2 so as not to contact with the blood vessel when the intracranial electrode 1 is placed on the brain surface in the electrode arrangement step (A) described later. Moreover, pressure application on the blood vessel by the silicone structure 2 can be prevented by forming the silicone structure 2 from the mold so as to provide an offset on the silicone structure 2 along a blood vessel (e.g. by forming a recess along the blood vessel). Note that, a size and a shape of the recess is not especially limited as long as a bulge on the brain surface due to the blood vessel can be contained in the recess. Moreover, the recess can be formed from the three-dimensional data by either directly fabricating the silicone structure 2 or by preparing the mold with the recess in advance.

The contrast medium is not especially limited, and may be a generally used contrast medium for MRI. One specific example of the contrast medium is gadolinium, but is not limited to this. Examples of such a contrast medium are a organic molecule, a metal ion, salt or chelate, a particle (especially an iron particle) or labeled peptide, protein, a polymer or a liposome, and the like. Moreover, the contrast medium may either be a tissue-nonspecific contrast medium or a target contrast medium. The tissue-nonspecific contrast medium is dispersed throughout among a whole body nonspecifically before metabolized and/or excreted after the administration. The target contrast medium specifically targets on a specific organ, a cell, or a tissue component of the body before metabolized and/or excreted after the administration.

Examples of a method for obtaining the three-dimensional data according to the brain image are computer systems such as CAD/CAM systems. However, the present invention is not limited to these examples. Moreover, after the three-dimensional data of the brain shape is obtained, positioning etc. of the electrodes 3 in the electrode arrangement step (A) (described later) may be performed based on the obtained three-dimensional data of the brain shape.

The mold is not especially limited as long as the silicone structure 2 can be formed by using the mold based on the three-dimensional data of the brain shape. Examples of the mold are (a) a mold in which a silicone solution is to be cast for forming a silicone structure 2 having a three-dimensional shape of the brain surface, (b) a mold on which a flat silicone sheet is to be attached for forming a silicone structure 2 having a three-dimensional shape of the brain surface, and (c) a mold whose surface is to be applied with silicone for forming a silicone structure 2 having a three-dimensional shape of the brain surface.

Among the above molds, the molds (b) and (c) are preferable because these molds can form a thin silicone structure 2. Note that, a thinner silicone structure 2 applies less pressure on the brain when the intracranial electrode 1 is placed on the brain surface.

In the structure formation step (A), as shown in FIG. 4, the silicone structure 2 is formed with use of a mold formed in the mold formation step (A). More specifically, the silicone structure 2 can be formed by such as press molding, transfer molding, injection molding, and cast molding. More specifically, in a case where the mold (a) is used, the silicone structure 2 is formed by casting the silicone solution in the mold, and subsequently curing the silicone solution in the mold. Moreover, in a case where the mold (b) is used, the silicone structure 2 is formed by press molding in which the flat silicone sheet prepared in advance is pressed, for example, on the heated mold so as to form the silicone sheet into the three-dimensional shape of the brain surface. Moreover, in a case where the mold (c) is used, the silicone structure 2 is formed by applying the silicone solution to the surface of the mold, and subsequently curing thus applied silicone solution. Note that, as described later, if a pair of molds which fit together is used in the step, a silicone structure having a more precise three-dimensional shape of the brain surface can be formed. This feature is described later.

In the electrode arrangement step (A), as shown in FIG. 4, the electrodes 3 are arranged on the silicone structure 2 formed in the structure formation step (A). A method for arranging the electrodes 3 on the silicone structure 2 is not especially limited. For example, the silicone structure 2 can be formed by a mold in which markings (such as holes) of positions for the electrodes 3 are provided. In the configuration, the markings are provided on the mold having the shape of the brain surface. That is, the markings are provided in consideration of the shape of the brain surface. Therefore, the electrodes 3 can be arranged on positions which do not reduce closeness between the silicone structure 2 and the brain surface.

Moreover, how to determine where to position the electrode 3 is not especially limited. It is preferable that in a case where the three-dimensional data of the brain shape includes positional information of blood vessels, the electrodes 3 are arranged so as not to contact with the blood vessels when the intracranial electrode 1 is placed on the brain surface according to the positional information.

Moreover, in a case where the electrodes 3 are arranged on both sides of the silicone structure 2, the electrodes 3 may be arranged on both sides of the silicone structure 2 either symmetrically or asymmetrically.

Moreover, in the present embodiment, the mold can be formed according to the three-dimensional data as well as with use of a three-dimensional printer. This allows easier and more precise formation of the mold.

The three-dimensional printer is not especially limited. A generally known three-dimensional printer may be used as appropriate. Examples of the three-dimensional printer are such as Zprinter (manufactured by Z Corporation, U.S.A.), and Dimension (manufactured by Marubeni Information Systems). However, the three-dimensional printer is not especially limited to these examples. Moreover, regarding a specific method for forming a mold with use of the three-dimensional printer, follow protocols attached to the three dimensional printers.

One example of a method for producing the silicone structure 2 is described below in detail. However, the present invention is not limited to the example.

In the method, first, a model having a brain shape is formed with use of three-dimensional data of the brain shape. In other words, a brain is reproduced with use of an artificial material. That is, in this specification, a brain reproduced with use of an artificial material is referred to as a "model". Note that, the model may be either a whole brain or a part of the brain.

A method for producing the model is not especially limited. A generally known method may be used as appropriate. For example, a three-dimensional printer or a three-dimensional optical molding machine may be used. However, the method is not limited to these examples. Moreover, although a material for the model is not especially limited, it is preferable that the material is not deformable under heated environment and negative-pressure environment. For example, the material is preferably acrylic, plastic, polyethylene, or dental cement (silicon). Use of these materials prevents deformation of the model in the mold formation step described later. This makes it possible to produce an intracranial electrode that applies less pressure on the brain.

Figure 6:
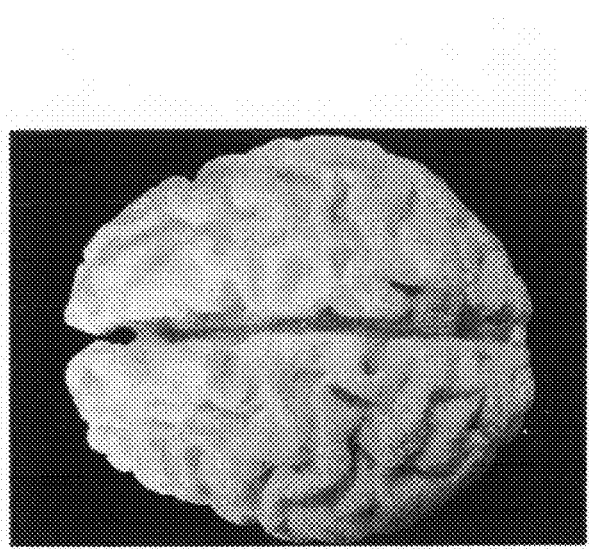
FIG. 6(a) is a view illustrating a model of sulcus emphatic type.
FIG. 6(b) is a view illustrating a model of sulcus smoothing type.
Figure 6:
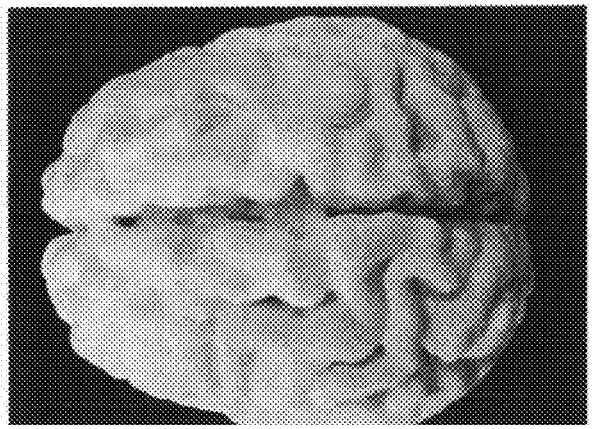

FIG. 6(*a*) and FIG. 6(*b*) show examples of the model. FIG. 6(*a*) shows the sulcus emphatic type model in which an outline of the sulcus is clearly reproduced. On the other hand, FIG. 6(*b*) shows the sulcus smoothing type model in which an outline of the sulcus is smoothly reproduced. The sulcus emphatic type model is suitable for use in producing an electrode for a deep part of the sulcus. The sulcus smoothing type model is suitable for use in producing an electrode for a superficial part of the sulcus. In the present invention, these models can be used as appropriate depending on a purpose.

Next, a mold is formed with use of the model. The mold is formed on the basis of a shape of the model. As a result, the mold is formed on the basis of the three-dimensional data of the brain shape. For example, the mold formation in this case may be carried out by (1) a method in which a sheet-shaped material is attached on a surface of the model with pressure or (2) a method in which a material is applied to the surface of the model, and subsequently pressing a supplemental mold, which covers the material, against the surface of the model with pressure.

Note that, the sheet-shaped material is not especially limited. However, the sheet-shaped material is preferably a plastic sheet, silicone sheet, parylene, polyethylene, or polypropylene. With the configuration, the sheet-shaped material can be easily deformed due to a change in temperature and/or pressure. This makes it possible to form a mold having a precise shape of the brain surface.

Moreover, the material to be applied is not especially limited. However, it is preferable that the material to be applied is acrylate resin, plaster, or dental cement (silicon). With the configuration, the material can be easily transformed according to a change in pressure, and also can keep the shape into which the material is once transformed. This makes it possible to form a mold having a precise shape of the brain surface.

First, a case where a mold is formed by the method (1) is explained as follows.

In the case where the mold is formed by the method (1), the sheet-shaped material is pressed against the surface of the model with pressure. That is, for example, positive pressure or negative pressure is applied on at least one of the sheet-shaped material and the model, whereby the sheet-shaped material and the model are attached together with pressure.

For example, first, the sheet-shaped material is processed into a cylindrical shape, and besides, one opening (e.g. top end of the cylindrical material) is sealed with another material. Then, the model is put inside the cylindrical material. Next, air inside the cylindrical material is sucked from the other opening (e.g. bottom end of the cylindrical material) so as to provide negative pressure inside. This causes the cylindrical material to get sucked inwardly, whereby the material is attached on a surface of the model. As a result, a mold having the shape of the brain surface can be formed easily. Note that, an apparatus for sucking air from inside of the cylindrical material is not limited. A generally used vacuum pump may be used as the apparatus.

In the case where the mold is formed by the method (1), it is preferable that the sheet-shaped material is heated up. This makes it easy to transform the sheet-shaped material, whereby a mold having a precise shape of the brain surface can be formed easily. A heating temperature to apply is not especially limited, and an appropriate temperature may be selected depending on the material to be heated. For example, the heating temperature is preferably in a range of 60° C. to 100° C., more preferably in a range of 60° C. to 80° C., and further preferably in a range of 60° C. to 70° C. This can prevents denature of the sheet-shaped material.

Next, a case where a mold is formed by the method (2) is explained as follows.

In the case where the mold is formed by the method (2), the material is applied on the surface of the model, and then a supplemental mold covering the material is pressed against the surface of the model with pressure. A method for applying the material is not especially limited. The material may be applied by a generally used method.

In the case where the mold is formed by the method (2), the material is sandwiched between the supplemental mold and the model. When the supplemental mold is pressed against the model with pressure, the material is also pressed to the model. As a result, a mold having a precise shape of the brain surface can be formed.

The supplemental mold may be made of any material as long as the supplemental mold can be pressed against the model with pressure. For example, it is preferable that the supplemental mold is made of latex or polyethylene.

Moreover, the supplemental mold is also not especially limited in terms of its shape. For example, the shape of the supplemental mold is preferable to be a sheet-shape or a container-shape which can contain the model wholly. However, the shape of the supplemental mold is not limited to the examples.

The supplemental mold is pressed against the surface of the model with pressure. That is, for example, positive pressure or negative pressure is applied on at least one of the supplemental mold and the model, whereby the supplemental mold and the model are attached together. For example, the supplemental mold is preferable to be pressed against the surface of the model with negative pressure. In this case, for example, the material is applied on the surface of the model, and then the model is put into a latex container (supplemental mold). Next, negative pressure is applied inside of the latex container by a vacuum pump, whereby the latex container is pressed against the surface of the model. In this case, the material is sandwiched between the latex container and the model, and therefore the material is also pressed to the model. As a result, a mold having the shape of the brain surface can be formed easily.

It is preferable to form another mold after forming a mold as above. In other words, it is preferable to form a pair of molds which fit together. With the configuration, a thin silicone structure 2 with a uniform thickness can be formed by the pair of molds.

The another mold should be attachable to a front side (e.g. a side which will contact with the surface of the model) or a back side (e.g. a reverse side of the side which will contact with the surface of the model) of the previously formed mold. Further, the two molds may either be identical or different. In a case where the two molds are identical, the two molds may be formed by the above explained method and used as a pair of molds. In a case where the two molds are different, the another mold may be formed with use of the previously formed mold. In this case, a method for forming the another mold is not especially limited. For example, the another mold can be formed by applying a material (for example, a plastic sheet, dental cement (silicon), or silicone) on the previously formed mold. With the method, a pair of molds with further closeness between one another can be formed.

It is preferable that a silicone structure 2 is formed with use of a pair of molds which is formed as above described. For example, a biocompatible material is arranged between the mold and the another mold. Then, the molds are pressed against one another with pressure, whereby pressure is applied on the biocompatible material between the molds. It is preferable to form a silicone structure 2 having a precise shape of the brain surface via the above described steps.

Figure 7:
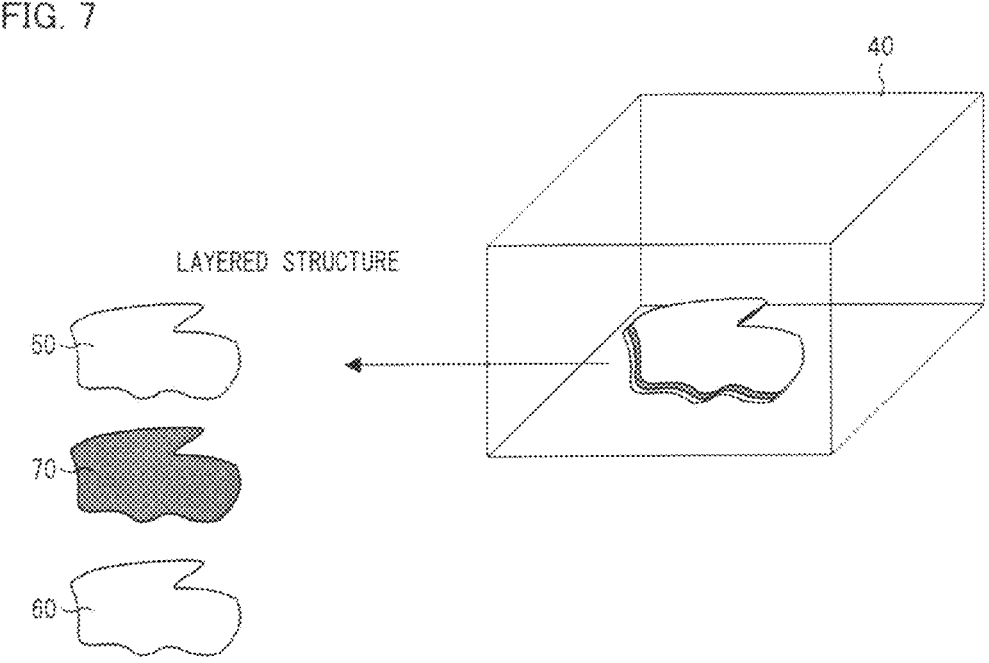
FIG. 7 is a view illustrating a method for forming a silicone structure with use of a pair of molds.

More specifically, as shown in FIG. 7, a biocompatible material is provided between a pair of molds (between interfaces of the molds). Then, an assembly of the molds and the biocompatible material is placed inside a flexible sealed container 40 (e.g. a bursiform container made of latex or polyethylene). Next, inside of the sealed container 40 is provided with a negative pressure state by a vacuum pump. With this, the sealed container 40 is contracted, and eventually, the pair of molds is attached together. In this case, a biocompatible material 70 arranged between a mold 50 and a mold 60 is extended along a shape of the molds. As a result, the biocompatible material is extended into the shape of the molds, that is, a shape of the brain surface. Note that, a specific configuration of the sealed container is not especially limited as long as its inside can be put in a negative pressure environment.

Moreover, it is preferable that the sealed container 40 is configured so that the assembly of the molds and the biocompatible contained inside therein can be heated up at a temperature of approximately 40° C. to 60° C. Note that, a specific configuration for heating is not especially limited. A generally known configuration can be used as appropriate.

Second Embodiment

Another embodiment of the present invention is explained below with reference to FIG. 3(a), FIG. 3(b), and FIG. 5. Note that, for convenience of explanation, the same referential numerals are given to members having the same functions as the members used in the first embodiment, and their explanation is omitted.

Figure 3:
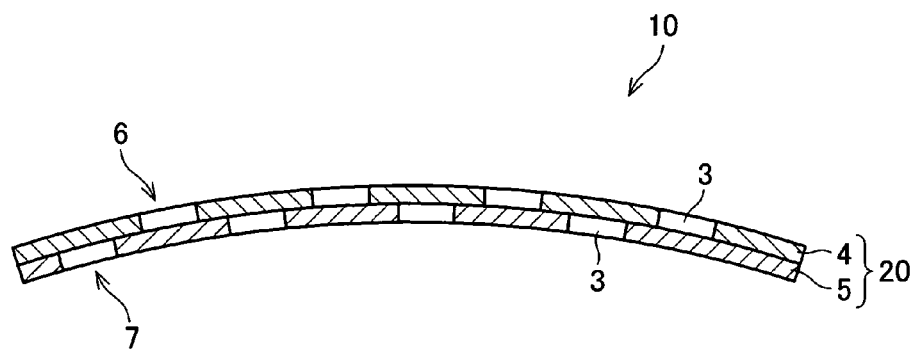
FIG. 3(a) is a cross-sectional view illustrating an intracranial electrode of another embodiment.
FIG. 3(b) is a cross-sectional view illustrating an intracranial electrode of another embodiment.
Figure 3:
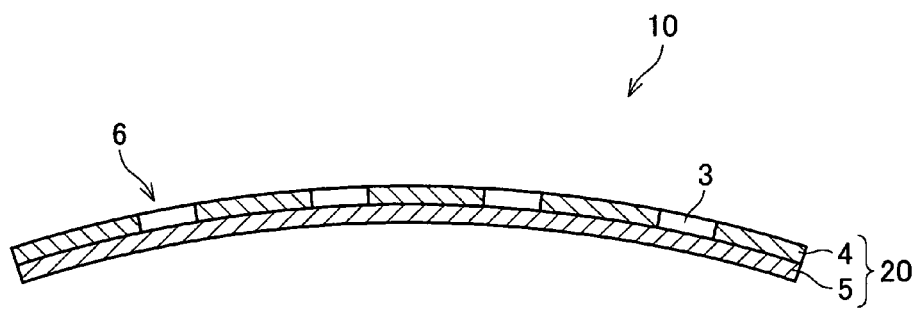

As shown in FIG. 3(a), an intracranial electrode 10 of the present embodiment includes a silicone structure 20 (structure) and an electrode 3. The silicone structure 20 has a two-layer structure in which a first silicone sheet 4 (a first layer; a sheet-shaped member) and a second silicone sheet 5 (a second layer; sheet-shaped member) are laminated.

In the present embodiment, the silicone structure 20 has a two-layer structure. However, the present invention is not limited to this, and the silicone structure 20 may have any multilayered (three-layer or more) structure. In such an embodiment, layers corresponding to the first silicone sheet 4 and the second silicone sheet 5 (which are explained in detail below) are outermost layers. Note that, another sheet arranged between the first silicone sheet 4 and the second silicone sheet 5 may be formed from either the same or a different material of the first silicone sheet 4 and/or the second silicone sheet 5. With use of the another sheet, a thickness of the silicone structure 20 can be adjusted as appropriate. That is, a thickness of the intracranial electrode 10 can be adjusted so that a front side and a back side of the intracranial electrode 10 can fit with the brain surface closely. Moreover, with use of the another sheet, it becomes easy to embed various wirings inside the intracranial electrode 10.

The first silicone sheet 4 has a hole 6. Similarly, the second silicone sheet 5 has a hole 7. The electrodes 3 are arranged in the hole 6 of the first silicone sheet 4, and also in the hole 7 of the second silicone sheet 5.

In the present embodiment, as shown in FIG. 3(a), the first silicone sheet 4 and the second silicone sheet 5 have the hole 6 and the hole 7 respectively. However, the present invention is not limited to this. That is, a hole may be formed in any one of the first silicone sheet 4 and the second silicone sheet 5 (e.g. see FIG. 3(b)).

In a cross-sectional view shown in FIG. 3(a), the first silicone sheet 4 has the four holes 6 and the second silicone sheet 5 has the four holes 7 respectively. However, the present invention is not limited to this. That is, the number of holes formed in the first silicone sheet 4 and the second silicone sheet 5 is not especially limited. Moreover, positions of holes formed in the first silicone sheet 4 and the second silicone sheet 5 are also not especially limited.

Formation of holes in the first silicone sheet 4 and the second silicone sheet 5 can be changed as appropriate according to a position and the number of an electrode 3 to be arranged.

Moreover, in the present embodiment, in a case where a plurality of the electrodes 3 is arranged, an interval between each electrode 3 is not especially limited. For more details, refer to the explanation in the first embodiment. Moreover, regarding arrangements of the electrodes 3 on the silicone structure 20 also, refer to the explanation in the first embodiment.

Further, in the present embodiment, the silicone structure 20 including the first silicone sheet 4 and the second silicone sheet 5 is provided as a base material. However, the present invention is not limited to this, and the base material may be made of a biocompatible material other than a silicone sheet. Regarding the biocompatible material, refer to the explanation in the first embodiment.

Next, a method for producing an intracranial electrode 10 is explained below with reference to FIG. 5. Note that, FIG. 5 shows the intracranial electrode 10 for placing in the sulcus. However, an intracranial electrode for placing on the brain surface can be produced with the same principle. That is, in producing the intracranial electrode 10 for placing in the sulcus, three-dimensional data of the sulcus shape is used in a mold forming step (B) described later. Similarly, in producing the intracranial electrode for placing on the brain surface, three-dimensional data of a brain surface shape may be used in the mold forming step (B) described later. As described above, depending on a position where an intracranial electrode is to be placed, three-dimensional data of a shape of the gyrus or sulcus surface, or the interhemispheric fissure or interlobar fissure surface may be used.

An intracranial electrode 10 can be produced by a method including the steps of: with use of three-dimensional data of a brain shape, forming molds for respectively forming two sheet-shaped structures that (i) have a three-dimensional shape of the brain surface and (ii) can be laminated together (hereinafter, referred to as a "mold forming step (B)"); with use of the molds, (i) forming a first silicone sheet 4 and a second silicone sheet 5 and (ii) forming a hole 6 in the first silicone sheet 4 and a hole 7 in the second silicone sheet 5 respectively (hereinafter, referred to as a "structure forming step (B)"); and (i) arranging electrodes 3 in regions where the hole 6 is formed in the first silicone sheet 4 and where the hole 7 is formed in the second silicone sheet 5, and (ii) attaching the first silicone sheet 4 and the second silicone sheet 5 together (hereinafter, referred to as a "electrode arrangement step (B)").

In the mold forming step (B), the molds are formed with use of the three-dimensional data of the brain shape. The molds are used for respectively forming two sheet-shaped structures that (i) have the three-dimensional shape of the brain surface and (ii) can be laminated together. For example, as shown in FIG. 5, the molds are formed with use of three-dimensional data of the sulcus shape. The molds are used for forming two sheets that (i) have a three-dimensional shape of the sulcus shape and (ii) can be laminated together.

As described above, in the intracranial electrode 10, the first silicone sheet 4 and the second silicone sheet 5 are laminated. That is, in the mold forming step (B), molds are formed for forming the first silicone sheet 4 and the second silicone sheet 5 which can be laminated together.

The both sheets have their own three-dimensional shapes. In some cases, therefore, it is difficult to laminate the first silicone sheet 4 and the second silicone sheet 5, when the both sheets have completely the same figure and size. On this account, it is preferable that the first silicone sheet 4 and the second silicone sheet 5 are formed to have different sizes from one another to the extent that they can be still laminated together.

Therefore, in the mold forming step (B), it is preferable to form two molds with use of the three-dimensional data of the brain shape for forming two sheets having three-dimensional shape of the brain surface. More specifically, as shown in FIG. 5, it is preferable that, with use of the three-dimensional data of the brain shape, two molds are formed respectively for forming the first silicone sheet 4 and for forming the second silicone sheet 5.

Such a method for forming, with use of the three-dimensional data, the two molds respectively for forming two sheets that (i) have a three-dimensional shape and (ii) can be laminated together is not limited. This can be easily performed by persons skilled in the art with use of a conventional method. For example, the two molds can be formed in accordance with the method explained in the first embodiment.

Figure 5:
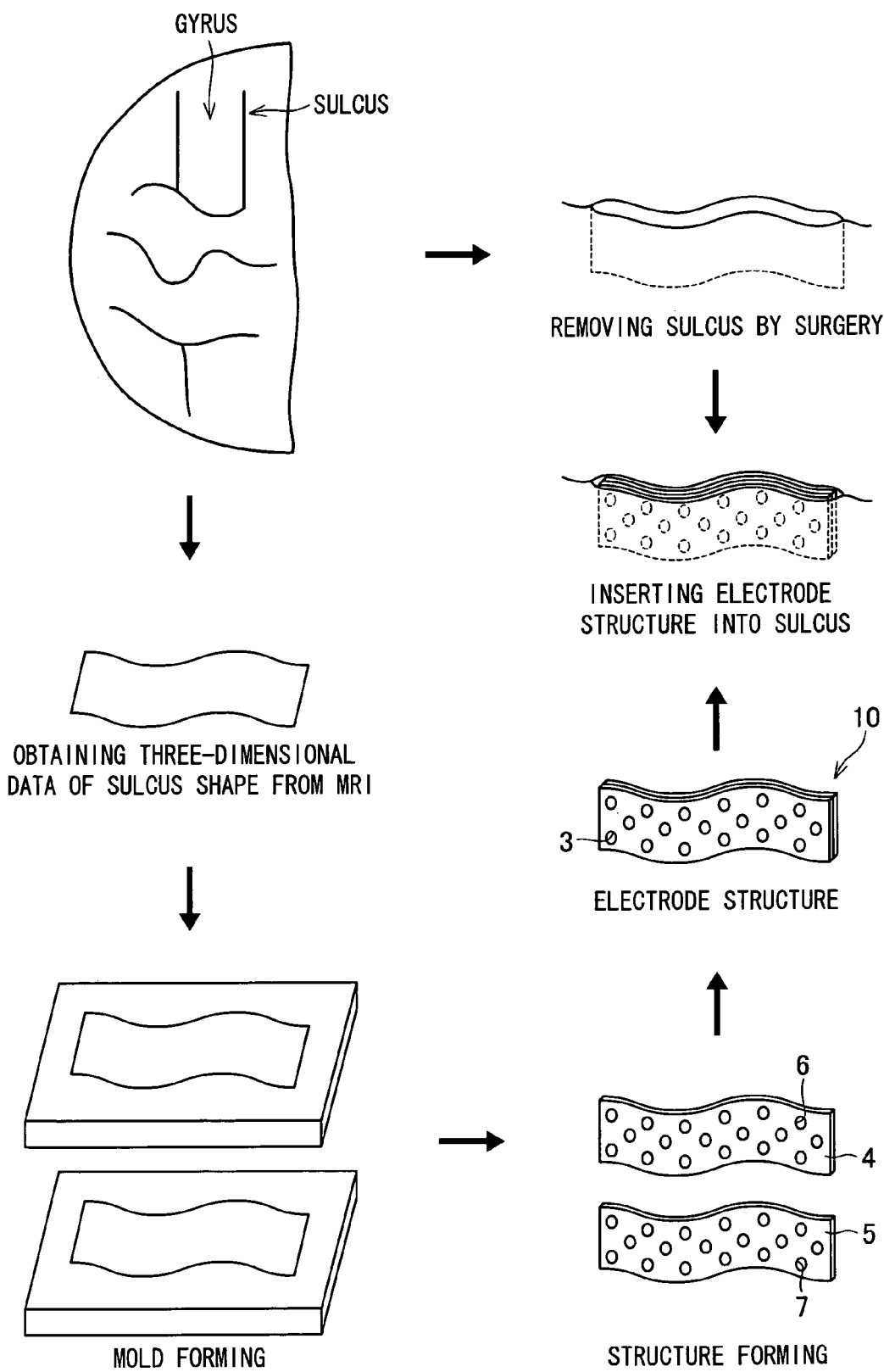
FIG. 5 is a view illustrating (i) steps of a method for producing an intracranial electrode of another embodiment, and (ii) how to insert the intracranial electrode into the brain.

In the structure forming step (B), first, as shown in FIG. 5, the first silicone sheet 4 and the second silicone sheet 5 are formed with use of the mold formed in the mold forming step (B). Although a method for forming the first silicone sheet 4 and the second silicone sheet 5 with use of the mold is not especially limited, the method explained in the first embodiment can be used.

Moreover, in the present embodiment, the molds for forming the first silicone sheet 4 and the second silicone sheet 5 can be formed based on the three-dimensional data with using a three-dimensional printer. With the configuration, a silicone structure 20 can be formed more easily and precisely.

The three-dimensional printer is not especially limited. A generally known three-dimensional printer may be used as appropriate. Examples of the three-dimensional printer are such as Zprinter (manufactured by Z Corporation, U.S.A.), and Dimension (manufactured by Marubeni Information Systems). However, the three-dimensional printer is not especially limited to these examples. Moreover, regarding a specific method for forming a mold with use of the three-dimensional printer, follow protocols attached to the three dimensional printers.

Thicknesses of the first silicone sheet 4 and the second silicone sheet 5 are not especially limited. In general, a thickness may be in a range of 0.02 mm to 0.1 mm. Moreover, thicknesses of the first silicone sheet 4 and the second silicone sheet 5 may either identical or different.

Note that, in the present embodiment, the silicone structure 20 of the intracranial electrode 10 has the two-layer structure. However, in a case where an intracranial electrode includes a silicone structure (i) having a multilayered (three-layer or more) structure and (ii) provided with an electrode, in the mold forming step (B), a mold may be formed for forming a plurality of silicone sheets that (i) can be laminated together and (ii) have a three-dimensional shape of the brain surface.

Next, in the structure forming step (B), as shown in FIG. 5, a hole 6 is formed in the first silicone sheet 4 and a hole 7 is formed in the second silicone sheet 5 respectively. The hole 6 and the hole 7 are formed in regions where electrodes 3 are to be arranged. Therefore, positions of the hole 6 on the first silicone sheet 4 and the hole 7 on the second silicone sheet 5 are determined corresponding to positions of the electrodes 3 in the intracranial electrode 10. Note that, positioning of the electrodes 3 in the intracranial electrode 10 may be performed in the same way as in the intracranial electrode 1 of the first embodiment.

In a cross-sectional view shown in FIG. 3(a), the first silicone sheet 4 and the second silicone sheet 5 respectively have four holes. However, the present invention is not limited to this. That is, a hole may be formed in any one of the first silicone sheet 4 and the second silicone sheet 5. Moreover, the number of holes formed in the first silicone sheet 4 and the second silicone sheet 5 is not especially limited.

Formation of holes in the first silicone sheet 4 and the second silicone sheet 5 may be changed as appropriate according to a position and the number of the electrodes 3 arranged on the silicone structure 20.

Further, a shape and a size of the hole 6 and the hole 7 formed in the first silicone sheet 4 and the second silicone sheet 5 are not especially limited, and may be changed as appropriate according to a shape, a size, an interval between electrodes, and the like of the electrode 3. More specifically, for example, sizes of the hole 6 and the hole 7 are preferable to be in a range of ø0.2 mm to ø3 mm, and more preferably, in a range of ø0.5 mm to ø1.5 mm.

Moreover, in the structure forming step (B), a method for forming the hole 6 in the first silicone sheet 4 and the hole 7 in the second silicone sheet 5 is not especially limited. A generally known method for forming a hole in a silicone sheet may be used. For example, a hole can be formed in advance in a mold for forming silicone sheets, or alternatively, after forming a silicone sheet by a mold, a hole can be formed in the silicone sheet.

Note that, in an embodiment where an intracranial electrode includes a silicone structure (i) having a multilayered (three-layer or more) structure and (ii) provided with an electrode, a plurality of silicone sheets that (i) can be laminated together and (ii) has a three-dimensional shape of the brain surface may be formed in the structure forming step (B). Moreover, a hole may be formed in an outermost silicone sheet when the plurality of silicone sheets is laminated.

In the electrode arrangement step (B), electrodes 3 are arranged in regions where the hole 6 is formed in the first silicone sheet 4 and where the hole 7 is formed in the second silicone sheet 5, and then, the first silicone sheet 4 and the second silicone sheet 5 are attached together.

A method for attaching the first silicone sheet 4 and the second silicone sheet 5 together is not especially limited. A generally known method, such as adhesive may be used for attaching.

Moreover, in the present embodiment, as shown in FIG. 3(a), the hole 6 and the hole 7 are formed not to overlap with one another when the first silicone sheet 4 and the second silicone sheet 5 are attached together. In such an embodiment, an electrode 3 that is arranged in a region of the hole 6 may be attached on the second silicone sheet 5. Similarly, an electrode 3 that is arranged in a region of the hole 7 may be attached on the first silicone sheet 4. With this configuration, the electrodes 3 can be fixed in the silicone structure 20 firmly.

Moreover, in another embodiment, the hole 6 and the hole 7 may overlap with one another when the first silicone sheet 4 and the second silicone sheet 5 are attached together. In this case, it is preferable that a size of the electrode 3 is larger than a diameter of the hole 6 and the hole 7 so that the hole 6 and the hole 7 can be covered with one electrode. Further, the first silicone sheet 4 and the second silicone sheet 5 are attached together while the first silicone sheet 4 and the second silicone sheet 5 hold the electrode 3 therebetween.

A method for attaching the first silicone sheet 4 and the second silicone sheet 5 together is not especially limited, and a generally used method may be used. More specifically, for example, the first silicone sheet 4 and the second silicone sheet 5 can be attached together by applying silicone adhesive to at least one of the first silicone sheet 4 and the second silicone sheet 5.

A thickness of thus obtained intracranial electrode 10 is not especially limited. However, the thickness is preferable to be as thin as possible for reducing pressure on the brain by the intracranial electrode 10 when the intracranial electrode 10 is placed on the brain surface. More specifically, the thickness is preferable to be 1.0 mm or less.

Note that, in the present embodiment, a wiring (not illustrated) connected with the electrode 3 is preferable to be sandwiched and held between the first silicone sheet 4 and the second silicone sheet 5.

Moreover, in an embodiment where an intracranial electrode includes a silicone structure (i) having a multilayered (three-layer or more) structure and (ii) provided with an electrode, a plurality of silicone sheets may be laminated so that a silicone sheet having the hole is arranged outermost in the electrode arrangement step (B). Further, after arranging the electrode in a region where the hole is formed, the plurality of silicone sheets may be attached together.

Figure 8:
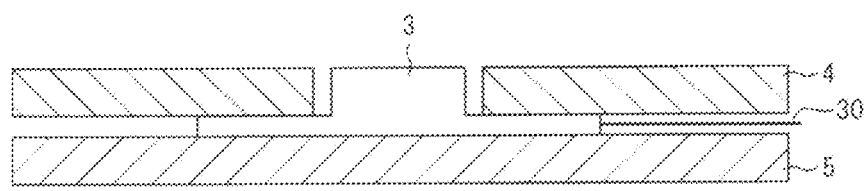
FIG. 8 is a cross-sectional view illustrating an intracranial electrode of another embodiment.

FIG. 8 shows an example of an intracranial electrode of the present invention. As shown in FIG. 8, the electrode 3 is preferable to have a multistage structure (e.g. two-stage structure). In this case, it is preferable that one of the stages (e.g. upper stage) has a size to be arranged inside the hole 6, and the other stage (e.g. lower stage) is larger than the hole 6. With the configuration, the electrode 3 can be fixed on the silicone structure 20 firmly. Moreover, a wiring 30 is preferable to be arranged between the first silicone sheet 4 and the second silicone sheet 5. This configuration can prevent the wiring 30 from contacting with the brain, whereby a safer intracranial electrode can be produced. Moreover, the (above-mentioned) other stage is preferable to be as thin as possible. In the configuration, no space is formed between the first silicone sheet 4 and the second silicone sheet 5, whereby a thinner intracranial electrode can be produced.

An electrode structure of the present invention is an electrode structure to be placed intracranially, wherein: the electrode structure is made of a biocompatible material; and an electrode is provided on a sheet-shaped structure having a three-dimensional shape of the gyrus or sulcus surface, or the interhemispheric fissure or interlobar fissure surface.

Regarding the electrode structure of the present invention, it is preferable that: the structure has at least a first layer and a second layer; the structure has a multilayered structure whose outermost layers are the first layer and the second layer respectively; at least one of the first layer and the second layer has at least one hole; and the electrode is arranged in a region of the hole.

In the electrode structure of the present invention, the electrodes may be arranged on both sides of the structure.

A method for producing an electrode structure of the present invention is a method for producing an electrode structure to be placed intracranially, including steps of: with use of three dimensional data of a brain shape, forming a mold for forming a sheet-shaped structure having a three-dimensional shape of the gyrus or sulcus surface, or the interhemispheric fissure or interlobar fissure surface; with use of the mold, forming a sheet-shaped structure which (i) is made of a biocompatible material and (ii) has the three-dimensional shape of the gyrus or sulcus surface, or the interhemispheric fissure or interlobar fissure surface; and arranging an electrode on the structure.

A method for producing an electrode structure of the present invention is a method for producing an electrode structure to be placed intracranially, including steps of: with use of three dimensional data of a brain shape, forming a mold for forming a plurality of sheet-shaped structures that (i) can be laminated together and (ii) has a three-dimensional shape of the gyrus or sulcus surface, or the interhemispheric fissure or interlobar fissure surface; with use of the mold, forming a plurality of sheet-shaped structures that (i) can be laminated together, (ii) is made of a biocompatible material and (iii) has the three-dimensional shape of the gyrus or sulcus surface, or the interhemispheric fissure or interlobar fissure surface; forming at least one hole in at least one of the plurality of sheet-shaped structures; laminating the plurality of sheet-shaped structures together so that the sheet-shaped structure having the hole is arranged outermost; arranging the electrode in a region where the hole is formed; and attaching the plurality of sheet-shaped structures together.

In the method for producing the electrode structure of the present invention, the three-dimensional data of the brain shape is preferable to be obtained based on a brain image obtained by magnetic resonance imaging.

As above, the intracranial electrode 1 and the method for producing the same, and the intracranial electrode 10 and the method for producing the same are explained as embodiments of an intracranial electrode and a method for producing the same of the present invention.

An intracranial electrode of the present invention is a sheet-shaped intracranial electrode having three-dimensional shape of the brain surface. Therefore, in a case where the intracranial electrode of the present invention is placed on the brain surface intracranially, pressure on the brain is reduced.

Especially, with a method for producing the intracranial electrode of the present invention, a custom-made intracranial electrode can be provided for individuals in whom the intracranial electrode is to be placed. That is, with the present invention, an intracranial electrode that fits a brain surface shape of each person, in whom the intracranial electrode is to be placed, can be produced.

An intracranial electrode of the present invention is an intracranial electrode to be placed intracranially. A method for placing the intracranial electrode intracranially is not especially limited. For example, in a case where the intracranial electrode is placed in the sulcus, as shown in FIG. 5, first, the sulcus in a region for placing the intracranial electrode is removed by a surgery from a person in whom the intracranial electrode is to be placed. Next, the intracranial electrode is inserted into the region where the sulcus is removed. With these steps, the intracranial electrode can be placed in the sulcus.

With the intracranial electrode of the present invention, for example, a localized examination for a brain function can be performed by placing the intracranial electrode in the sulcus, and subsequently applying electrical stimulation to inside of the sulcus by the intracranial electrode.

Moreover, new brain treatment with electrical stimulation can be provided by placing the intracranial electrode in the sulcus, and subsequently applying electrical stimulation to inside of the sulcus by the intracranial electrode. More specifically, for example, this can be used in brain treatment with electrical stimulation for intractable blocked pain. Further specifically, a palliative treatment for intractable blocked pain can be performed effectively by placing the intracranial electrode in the central sulcus and stimulating the primary motor area. As described above, the intracranial electrode of the present invention can be used as a therapeutic electrode.

Further, the intracranial electrode of the present invention can be used as an electrode applied to a brain machine interface (a technology in which brain activity is decoded from a brain signal, and the result is used in functional restoration of the brain). That is, the present invention includes a device such as a medical equipment having the intracranial electrode of the present invention.

More specifically, such a device includes, for example, (1) a motility function rehabilitation device, (2) a visual function rehabilitation device, and (3) a language function rehabilitation device.

In the motility function rehabilitation device, the intracranial electrode is placed in the central sulcus. The central sulcus has the primary kinesthetic sensorial area. Therefore, a motion intention and a motion content can be decoded and reproduced by measuring a brain signal in the kinesthetic sensorial area efficiently with use of the intracranial electrode.

Moreover, in the visual function rehabilitation device, the intracranial electrode is placed in the calcarine sulcus of brain. The calcarine sulcus of brain has the primary visual area. Therefore, an effective visual sense can be given to a severe visually-impaired person by applying electrical stimulation to the primary visual area efficiently with use of the intracranial electrode.

Further, with the language function rehabilitation device, a communication function can be given to a speech-impaired person due to such as high-spinal cord injury.

As described above, the intracranial electrode of the present invention is an intracranial electrode to be placed intracranially wherein an electrode is provided on a sheet-shaped structure which (i) is made of a biocompatible material, and (ii) has a three-dimensional shape of the gyrus or sulcus surface, or the interhemispheric fissure or interlobar fissure surface.

With this configuration, the intracranial electrode of the present invention can be placed on the gyrus or sulcus surface, or the interhemispheric fissure or interlobar fissure surface, with less pressure applied on the brain. Moreover, this provides an effect that a brain signal from the gyrus or sulcus surface, or the interhemispheric fissure or interlobar fissure surface, can be detected without causing disturbance or damage to the brain.

Moreover, the structure is made of a biocompatible material, whereby the structure is not toxic to a living body.

Moreover, the intracranial electrode of the present invention has a shape consistent with a brain surface shape, whereby fits with the brain surface closely. With the configuration, a brain signal can be detected precisely, and besides, desired electrical stimulation can be applied to the brain surface precisely.

As described above, the present invention provides an intracranial electrode wherein an electrode is provided on a sheet-shaped structure which (i) is made of a biocompatible material and (ii) has a three-dimensional shape of the gyrus or sulcus surface, or the interhemispheric fissure or interlobar fissure surface. With the intracranial electrode, a brain signal from the gyrus or sulcus surface, or the interhemispheric fissure or interlobar fissure surface can be detected, and electrical stimulation can be applied to the gyrus or sulcus surface, or the interhemispheric fissure or interlobar fissure surface.

Therefore, the present invention can be not only used as a medical electrode for studying brain functions, but also widely applied to: a therapeutic electrode such as a therapeutic electrode for pain; various kinds of medical equipments, which are provided with an intracranial electrode, such as a motility function rehabilitation device, a visual function rehabilitation device, a language function rehabilitation device, and a device for brain treatment with electrical stimulation; and a manufacturing field of those.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

The invention claimed is:

1. A method for producing an intracranial electrode comprising the steps of:
    obtaining three-dimensional data of a brain shape;
    with use of the three-dimensional data, forming a sheet-shaped mold having a three-dimensional shape of a gyrus or sulcus surface, or an interhemispheric fissure or interlobar fissure surface;
    with use of the mold, forming a sheet-shaped structure which (i) is made of a biocompatible material and (ii) has the three-dimensional shape of the gyrus or sulcus surface, or the interhemispheric fissure or interlobar fissure surface; and
    arranging an electrode on at least one side of the structure.

2. The method as set forth in claim 1, further comprising the steps of:
    forming another mold which fits closely with a front side or a back side of the mold;
    arranging the biocompatible material between the mold and the another mold;
    and forming the sheet-shaped structure by pressing the mold and the another mold against each other with pressure.

3. The method as set forth in claim 1, wherein: the mold is formed by attaching a sheet-shaped material to a surface of a model with pressure, the model having the brain shape formed with use of the three-dimensional data.

4. The method for producing an intracranial electrode as set forth in claim 1, wherein: the mold is formed by applying a material to a surface of a model having the brain shape formed with use of the three-dimensional data, and subsequently pressing a supplemental mold to the surface of the model with pressure, the supplemental mold covering the material.

5. The method for producing an intracranial electrode as set forth in claim 1, wherein: the mold is formed by a three-dimensional printer or a three-dimensional optical molding machine with use of the three-dimensional data.

6. The method for producing an intracranial electrode as set forth in claim 1, further comprising the steps of:
    with use of the mold, forming a first sheet-shaped member which (i) is made of a biocompatible material and (ii) has a three-dimensional shape of the gyrus or sulcus surface, or the interhemispheric fissure or interlobar fissure surface;
    with use of the mold, forming a second sheet-shaped member which (i) is made of a biocompatible material and (ii) has a three-dimensional shape of the gyrus or sulcus surface, or the interhemispheric fissure or interlobar fissure surface; and
    forming the sheet-shaped structure by attaching the first sheet-shaped member and the second sheet-shaped member together.

7. The method for producing an intracranial electrode as set forth in claim 6, wherein: the mold for forming the first sheet-shaped member is different from the mold for forming the second sheet-shaped member.

8. The method for producing an intracranial electrode as set forth in claim 1, wherein: the three-dimensional data of the brain shape is obtained based on a brain image obtained by magnetic resonance imaging.

9. The method for producing an intracranial electrode as set forth in claim 1, wherein: the electrode is provided at a position at which the electrode will not contact with a blood vessel.

10. The method for producing an intracranial electrode as set forth in claim 1, further comprising the step of: in the sheet-shaped structure, forming a recess at a position which corresponds to a blood vessel on the brain surface.

11. An intracranial electrode, comprising:
    a structure which (i) has a sheet-shape and (ii) is made of a biocompatible material, the structure having a three-dimensional shape of a gyrus or sulcus surface, or an interhemispheric fissure or interlobar fissure surface; and
    the structure including at least one electrode.

12. The intracranial electrode as set forth in claim 11, wherein:
    the structure includes at least a first layer and a second layer;
    the structure has a multilayered structure whose outermost layers are the first layer and the second layer respectively;
    at least one hole is formed in at least one of the first layer and the second layer;
    and the electrode is provided in the hole.

13. The intracranial electrode as set forth in claim 11, wherein: the electrodes are provided on both sides of the structure.

14. The intracranial electrode as set forth in claim 11, wherein: the structure has a region in which a plurality of electrodes is arranged in high density; and
    intervals between the adjacent electrodes in the region are in a range of 0.3 mm to 10 mm.

15. The intracranial electrode as set forth in claim 11, wherein: the electrode is provided at a position at which the electrode will not contact with a blood vessel.

16. The intracranial electrode as set forth in claim 11, wherein: in the sheet-shaped structure, a recess is formed at a position which corresponds to a blood vessel on the brain surface.

17. Brain treatment with electrical stimulation, wherein: electrical stimulation is applied to a gyrus or sulcus surface, or an interhemispheric fissure or interlobar fissure surface by using the intracranial electrodes as set forth in claim 11.

* * * * *